US009867971B2

(12) United States Patent
Gogly et al.

(10) Patent No.: US 9,867,971 B2
(45) Date of Patent: Jan. 16, 2018

(54) DEVICE FOR ADMINISTERING CELLS AND CELL-THERAPY METHODS USING SAID DEVICE

(75) Inventors: Bruno Gogly, Hondevilliers (FR); Bernard Coulomb, Igny (FR); Antoine Lafont, Paris (FR)

(73) Assignees: ASSISTANCE PUBLIQUE—HOPITAUX DE PARIS, Paris (FR); INSERM, Paris (FR); UNIVERSITE PARIS DESCARTES, Paris (FR)

( * ) Notice: Subject to any disclaimer, the term of this patent is extended or adjusted under 35 U.S.C. 154(b) by 235 days.

(21) Appl. No.: 12/682,585

(22) PCT Filed: Oct. 9, 2008

(86) PCT No.: PCT/EP2008/063550
§ 371 (c)(1),
(2), (4) Date: Jun. 18, 2010

(87) PCT Pub. No.: WO2009/047300
PCT Pub. Date: Apr. 16, 2009

(65) Prior Publication Data
US 2010/0292670 A1 Nov. 18, 2010

Related U.S. Application Data

(60) Provisional application No. 60/978,518, filed on Oct. 9, 2007.

(51) Int. Cl.
*A61M 29/00* (2006.01)
*A61M 31/00* (2006.01)
*A61K 9/70* (2006.01)
*A61F 2/07* (2013.01)

(52) U.S. Cl.
CPC ......... *A61M 31/002* (2013.01); *A61K 9/7023* (2013.01); *A61F 2/07* (2013.01); *A61F 2250/0003* (2013.01); *A61F 2250/0068* (2013.01)

(58) Field of Classification Search
CPC ...... A61M 25/1011; A61M 2025/1013; A61M 1/0088; A61M 39/0208; A61M 2025/1052; A61M 25/104; A61M 31/002; A61F 2250/0003; A61F 2250/0068; A61F 2/07
USPC ...... 604/502, 104, 246, 305, 101.03, 101.02
See application file for complete search history.

(56) References Cited

U.S. PATENT DOCUMENTS

| | | | | |
|---|---|---|---|---|
| 5,985,307 | A * | 11/1999 | Hanson et al. | 424/423 |
| 6,682,555 | B2 * | 1/2004 | Cioanta et al. | 623/1.21 |
| 2002/0034505 | A1* | 3/2002 | Nabel et al. | 424/94.2 |
| 2007/0112330 | A1* | 5/2007 | Palasis | 604/509 |
| 2010/0268323 | A1* | 10/2010 | Sullivan | A61F 2/07 623/1.15 |

* cited by examiner

*Primary Examiner* — Rebecca E Eisenberg
(74) *Attorney, Agent, or Firm* — Hershkovitz & Associates, PLLC; Abe Hershkovitz

(57) ABSTRACT

The present invention relates to a device (2) for cell therapy, said device being designed to be applied on a living tissue and having at least a tight preferably biocompatible first wall (22), designed to form a cavity (24) between said wall and said tissue, and further comprising means (7) to feed a healing substance in said cavity.

9 Claims, 3 Drawing Sheets

DEVICE FOR ADMINISTERING CELLS AND CELL-THERAPY METHODS USING SAID DEVICE

The present application claims the benefit of U.S. Provisional Application No. 60/978,518 filed Oct. 9, 2007.

FIELD OF THE INVENTION

The present invention relates to a device suitable for administering cells at sites of an individual body where they are needed. The invention also relates to different therapeutical use of such a device.

BACKGROUND OF THE INVENTION

Cell therapy intends to correct defects, for example skin or vascular defects, in tissues of an individual by administering cells suitable to cure said defect to the individual.

Various methods for administering cells at a defect site exist. For instance, in the case of skin wounds or burns in an individual, autologous dermal fibroblasts can be cultivated on a biocompatible lattice which is then grafted onto the individual e.g. as described by Coulomb et al. (1998) *Plast. Reconstr. Surg.* 101:1891-1903. The main drawback associated to this technique lies in the long culture time necessary for the dermal fibroblast to colonize the lattice prior to implantation.

In the case of the treatment of vascular defects, the cells can be injected at the site of defect for instance using an angioplasty balloon catheter provided with micro needles (e.g. Infiltrator®). However, the drawback of this technique is that blood circulation is interrupted in the vessel during administration of the cells. Besides, this technique is not adapted for protocol in large vessels and may be harmful by itself.

Accordingly, it is an object of the invention to provide devices and methods capable of overcoming these drawbacks.

SUMMARY OF THE INVENTION

The present invention thus relates to a device for cell therapy, said device being designed to be applied on a living tissue and having at least a tight preferably biocompatible first wall, designed to form a cavity between said wall and said tissue, and further comprising means to feed a healing substance in said cavity.

In an embodiment of the above-defined device said feeding means comprise a valve to connect a feeding catheter to supply the substance, and, after feeding, to prevent the supplied substance to leak through feeding means.

In another embodiment of the above-defined device there are at least two valves, one at each of two substantially opposite ends of the device.

In another embodiment of the above-defined device, a catheter portion is provided to branch, in a removable way, the feeding catheter.

In another embodiment, the above-defined device further comprises a second wall with at least a porous part, the cavity being provided between said first and second walls, the healing agent being to be administered through said porous part, which is preferably made of a micro-perforated material, of a weed fabric, and/or of collagen, said wall second wall being biocompatible and preferably bioresorbable.

In another embodiment of the above-defined device, at least one of the first and second walls, preferably the first wall, comprises on a face turned toward the other of the two walls, a pattern in relief.

In another embodiment, the above-defined device is substantially cylindrically shaped, the first wall being a tight internal wall, and the second wall being an external wall. Preferably, the external wall has two tight annular ends and, between said ends, said porous part. Besides, expansion means are also preferably provided to the above-defined device to bring an outward radial pressure on the internal wall so as to urge said internal wall toward said external wall, and tend to provide a radial expansion on the device. Preferably, the expansion means are resilient means. Also preferably, the expansion means are a type of stent.

In another embodiment, the above-defined device is substantially flatly shaped. In that case it is preferred that the porous portion of the second wall is surrounded by a peripheral tight portion, said peripheral portion preferably having an adhesive face to maintain said porous part against a skin wound.

In yet another embodiment of the above-defined device, the healing agent filled up in the cavity is a suspension of cells, preferably gingival fibroblasts.

In a further embodiment, the above-defined device is for use in the treatment of defects of biological conduits, such as vascular defects, of hollow organs, or of flat wounds.

The present invention also relates to gingival fibroblasts for use in the treatment of defects of biological conduits, such as vascular defects, of hollow organs, or of flat wounds, wherein the gingival fibroblasts are administered with a device as defined above.

The present invention also relates to the use of a device as defined above, for the manufacture of an intraluminal implant intended for the treatment of defects of biological conduits or of hollow organs or for the manufacture of a plaster intended for the treatment of flat wounds.

In an embodiment, the present invention notably relates to the use of a device as defined above, for the manufacture of an intravascular implant intended for the treatment of vascular defects.

The present invention also relates to the use of cells, for instance of gingival fibroblasts, for the manufacture of a medicament intended for the treatment of defects of biological conduits or of hollow organs, or for the treatment of flat wounds, wherein the cells are administered with a device as defined above.

In an embodiment, the present invention notably relates to the use of cells, for instance of gingival fibroblasts, for the manufacture of a medicament intended for the treatment of vascular defects, wherein the cells are administered with a device as defined above.

The present invention also relates to a method for treating a patient in need of cell therapy, wherein a therapeutically effective quantity of cells suitable for said cell therapy are administered with a device as defined above.

The present invention further relates to a method for treating defects of biological conduits or of hollow organs in a patient, in particular vascular defects, comprising:
positioning a device as defined above at a site of defect of a biological conduit or of a hollow organ, in particular at a site of vascular defect;
filling said device with a suspension of cells suitable to treat said defect, in particular gingival fibroblasts; and
maintaining the device in place at least for a time sufficient for a therapeutically effective quantity of cells to have migrated in direction of the defect and/or for the cells to have exerted a therapeutically effective paracrine effect.

Similarly, the invention also relates to a method for treating flat wounds, in particular skin wounds, in a patient, comprising
positioning a device as defined above at a site of flat wound, in particular at a site of skin wound;
filling said device with a suspension of cells suitable for treating said wound, in particular gingival fibroblasts; and maintaining the device in place at least for a time sufficient for a therapeutically effective quantity of cells to have migrated in direction of the wound and/or for the cells to have exerted a therapeutically effective paracrine effect.

In a preferred embodiment, the above-defined device is suitable for a single use only, i.e. it cannot be re-used a second time when it has already been used for cell therapy in an individual.

DETAILED DESCRIPTION OF THE INVENTION

Definitions

Figure 1:
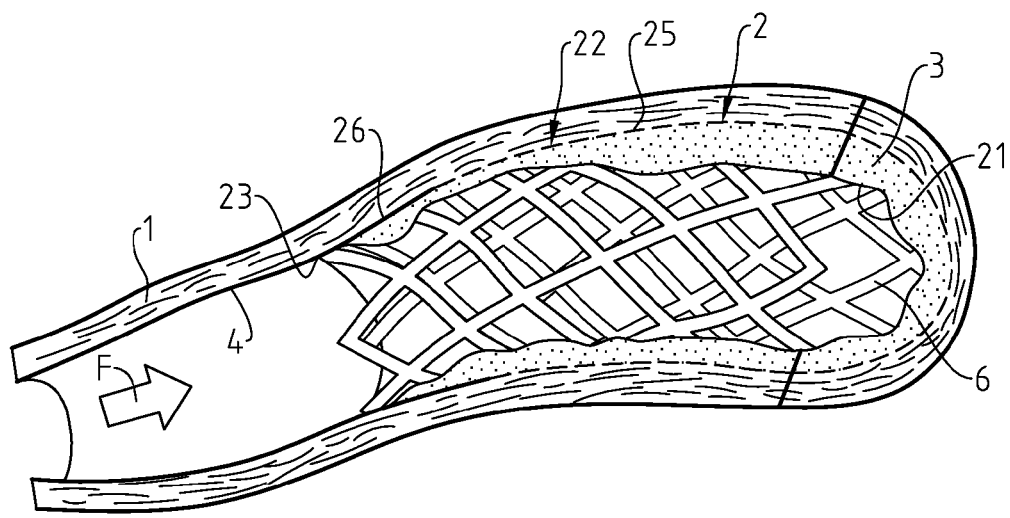
FIG. 1 is a partially longitudinally cut of diagrammatic perspective view of a first embodiment device according to the invention in position in a blood vessel.

As intended herein "cell therapy", for example using gingival fibroblasts, relates to the correction of defects, for example vascular defects or skin wounds, in tissues of an individual by administering cells suitable to cure said defect to said individual.

As intended herein "healing agent" relates to any agent who has the ability to promote, accelerate, or improve wound healing. The agent can be a compound in solution, such as a compound selected from the group constituted of growth factors and cytokines. The agent can also be a cell suspension.

As intended herein a "cell suspension" for a cell therapy relates to a liquid composition comprising cells in a medium suitable to sustain survival and optionally growth of these cells. Such media are well known to the man skilled in the art.

As intended herein a "biological conduit" relates to any conduit which can be found in a human or an animal body which function is to conduct fluids or gases within the body. Biological conduits notably encompass the vascular, digestive, respiratory or uro-genital conduits.

As intended herein a "defect of a biological conduit" relates to a lesion or a disease of the internal wall of said conduit.

As intended herein a "hollow organ", or a cavitary organ, relates to any organ which comprises a cavity. Hollow organs notably encompass the heart and vesicular organs, such as the biliary vesicule or the bladder.

As intended herein a "defect of a hollow organ" relates to a lesion or a disease of the internal wall of said conduit.

In particular, as intended herein a "vascular defect" relates to a defect of vascular walls, preferably of arterial walls, which occurs upon abnormal cicatrisation of lesions of these walls. The lesions are of various origins, such as hypoxia, lipid overload, hemodynamic factors, atheroma, or hypertension. Abnormal cicatrisation notably results from disequilibrium between degradation and synthesis of the extracellular matrix, which disequilibrium induces pathological vascular remodelling. Manifestations of abnormal cicatrisation particularly encompass vascular enlargement (e.g. aneurism), loss of elastin and vascular constriction (e.g. stenosis, occurring in the course of atherogenesis, or restenosis, in particular post-angioplasty restenosis).

As intended herein a "flat wound" relates to any wound afflicting a flat surface of a tissue. Flat wounds notably encompass skin wounds.

As intended herein a "skin wound" relates to any rupture of the epidermis and/or the dermis.

Skin wounds according to the invention can be particularly selected from the group consisting of chronic wounds, pressure ulcers, venous ulcers, skin burns and accidental or medically-related wounds, including irradiation.

Furthermore skin wounds according to the invention can also be surgical wounds, i.e. wounds voluntarily made during a surgical procedure. Such surgical wounds notably encompass wounds occurring in the course of plastic and reconstructive surgery or scar revision wounds (e.g. hypertrophic scars).

The plastic and reconstructive surgery procedures according to the invention can be of any type, e.g. breast surgery, abdominal surgery, nose surgery, ear surgery, or removal of skin wounds. As intended herein, skin wounds relate to an abnormal skin formation found in genetically predisposed individuals or to the consequences of an abnormal skin development during embryogenesis, and notably comprise giant naevi, cheiloschisis, and keloids.

As intended herein "treating a flat wound" or "treating a skin wound" relates to the promotion, the acceleration, or the improvement of healing at the wounded site, in particular to the formation of a functional skin at the wounded site.

As intended herein a "functional skin" relates to skin having in particular recovered its mechanical properties and its barrier function, with respect to non-wounded skin areas.

As intended herein "gingival fibroblasts" relate to mesenchymal cells which are capable of migrating, adhering and proliferating within the soft connective tissues of the gum, thereby maintaining the integrity of the gingival tissue which is exposed to numerous aggressions, such as mechanical stresses, bacterial infections, or pH and temperature variations. Gingival fibroblasts are in particular described in Gogly et al., (1997) *Clin. Oral Invest.* 1:147-152; Gogly et al. (1998) *Biochem. Pharmacol.* 56:1447-1454; and Ejeil et al. (2003) *J. Periodontol.* 74:188-195.

Depending on environmental conditions, gingival fibroblasts are capable to modulate their phenotype, and to respond by proliferating, migrating, synthesising matrix components or matrix-related enzymes.

Gingival fibroblasts synthesise collagens (e.g. types I, III, V, VI, VII, XII), elastic fibers (oxytalan, elaunin and elastin), proteoglycans and glycosaminoglycans (e.g. decorin, biglycan), glycoproteins (e.g. fibronectin, tenascin). Simultaneously, gingival fibroblasts synthesise enzymes that are able to degrade the macromolecular compounds (matrix metelloproteinases; MMPs), but also enzymes inhibiting active forms of MMPs (Inhibitors of metalloproteinases; TIMPs). Gingival fibroblasts are thus important actors of extracellular matrix remodelling.

Procedures for taking, culturing and preserving gingival fibroblasts are well known to the man skilled in the art and are particularly described in Naveau et al. (2006) *J. Periodontol.* 77:238-47.

PREFERRED EMBODIMENTS

FIGS. 1-4 illustrate a first embodiment for a device according the invention, this embodiment being adapted to the treatment of vascular defects.

Figure 2:
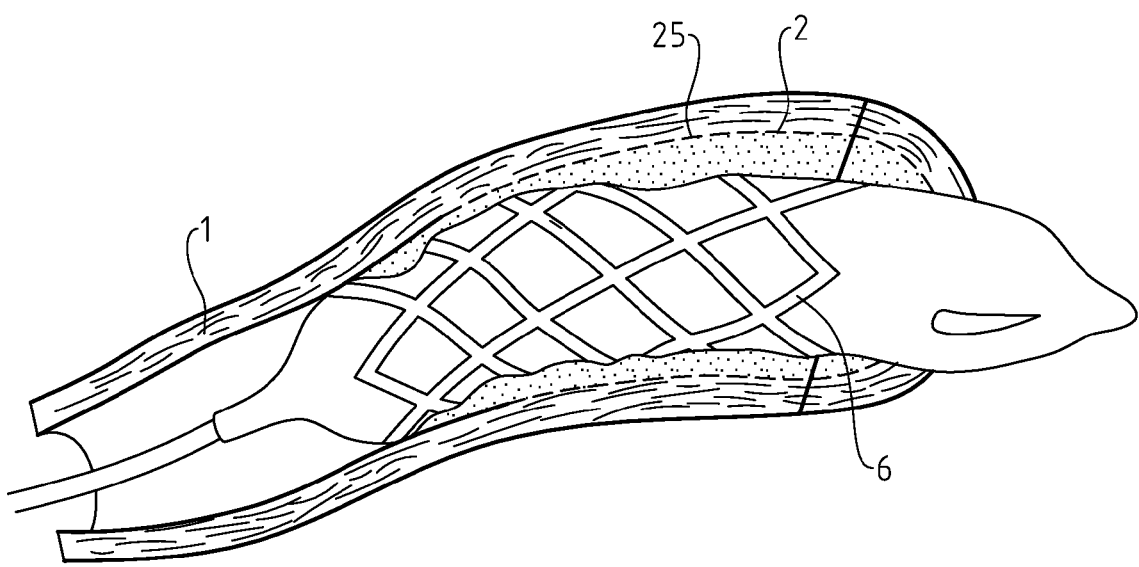
FIG. 2 is a figure similar to FIG. 1, showing the use of a balloon to set up the device according to the invention.
Figure 3:
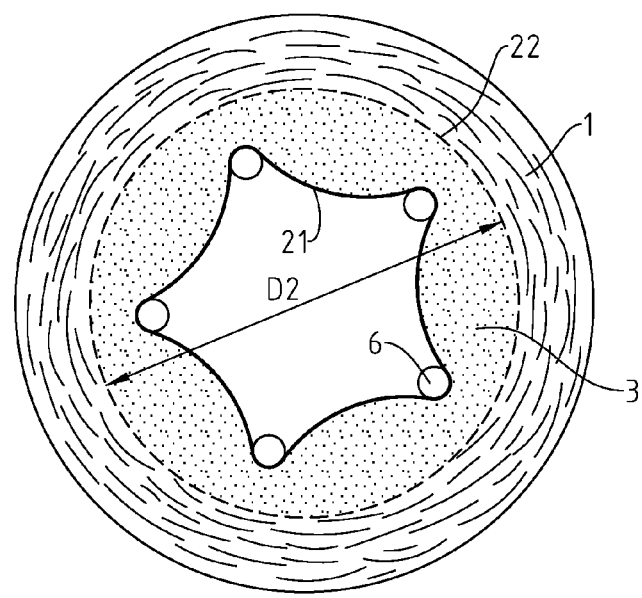
FIG. 3 is a diagramatic transversal cut of the device of FIG. 1 or 2.
Figure 4:
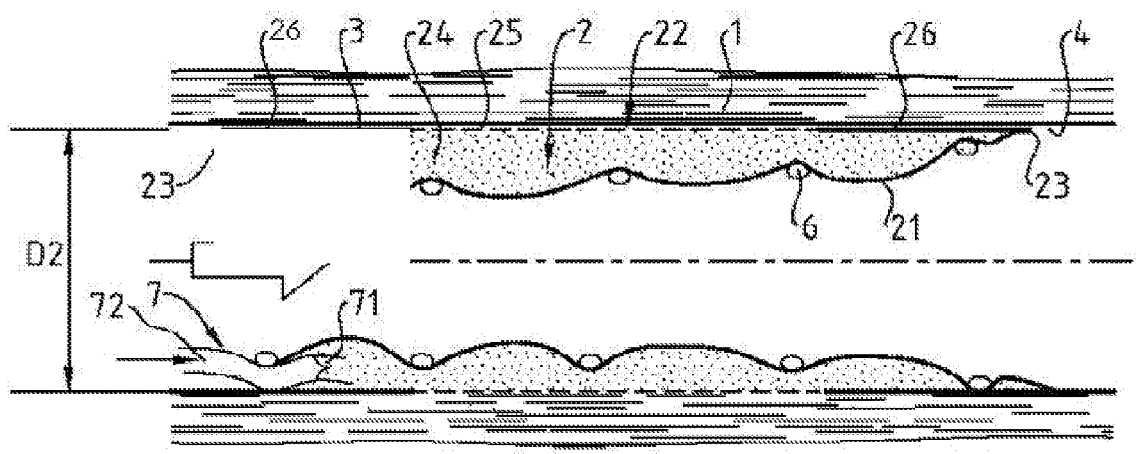
FIG. 4 is a diagramatic longitudinal cut of the same device.

In FIGS. 1, 2 and 4, a blood vessel 1 is illustrated longitudinally cut, and on FIG. 3, transversally cut. A healing device 2 is disposed in the internal cavity of said vessel, along a defect site thereof.

The device 2 of FIG. 1-4 is of a generally tubular shape. It is expandable, so as it may be moved toward the defect site of the vessel, and then expanded so that its external diameter D2 match with the internal diameter of the vessel. Of course, this external diameter may vary all along the device, as a vessel has neither a constant diameter nor a perfect circular section.

The device comprises two walls 21,22 substantially tubular, one first wall 21, and one wall 22, respectively internal and external. The two walls are joined together at their common longitudinal ends 23, so that a cavity 24 is provided between the two walls. The cavity is suitable to contain a substance 3 with a healing agent, preferably under pressure.

The internal wall 21 is tight, so that the substance 3, shown as dots on the figures, is prevented to leak through the internal wall 21. It can be biodegradable.

On the contrary, the external wall, in a part 25 in contact with the wounded portion of the vessel, is a porous portion. This porous portion 25 is designed to let the healing agent seep through, to dispense it to the wounded area.

Beyond each longitudinal end of this porous portion 25, at longitudinal ends of the external wall 22, there are two tight portions 26. As these tight portions 26 are provided to be in contact with the wall 4 of the vessel, they prevent leaking, between the external wall 22 and the wall 4, of the agent seeping through porous portion 25.

As the device 2 is substantially tubular, when in place, it allows blood flow F during treatment. Then the intervention is less a trauma for the patient, and needs far less time and equipment.

As particularly shown on FIG. 1, the device 2 can comprise a stent 6 which can be used to set the radial extension of the device, and along treatment, maintain the extension of the device. In particular, the stent 6 is designed to maintain the external wall 22 substantially in contact with the wall 4 of the vessel, even when the cavity is emptying. Regarding the stent used to widen blood vessels, such a stent 6 can be of a lighter design, as less strong is needed to maintain the device 2 than to widen a vessel.

These stents can be auto-expandable, for example, it can be maintained at a reduced diameter a temperature of the operating room, for example at 20 or 25° C., then, using a memory of form, gain a larger diameter, the temperature of the patient's body, around 37° C.

As shown on FIG. 2, if not auto-expendable, the stent may be first expanded by a balloon, the remaining resilience of the stent allowing compensating the emptying of the cavity, by urging internal wall 21 toward external wall 22.

When the device is released in place, the cavity is generally empty. The device, as shown in FIG. 4, is then provided with means 7 to fill up the cavity. Those means comprise a pipe portion 72 to connect a feeding catheter (not shown) and a valve 71, to prevent leaking of substance, through the pipe portion 72, after filling of the cavity 3. Optionally, the device can be provided with a second filling means which comprises a discharge pipe portion and a discharge valve; when a sufficient pressure is reached in the cavity 24 the valve is designed to open, so that, in particular, an excess quantity of substance is released through the discharge pipe.

Figure 5:
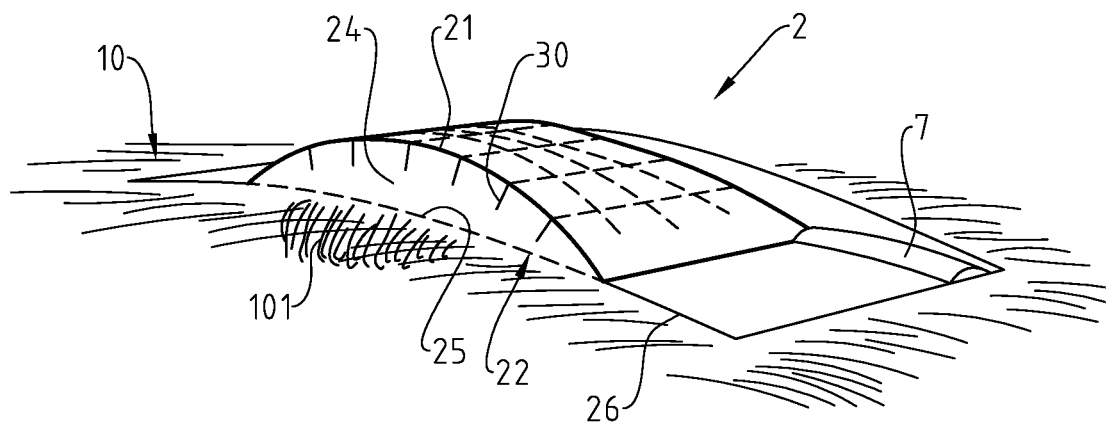
FIG. 5 is a cut of diagrammatic perspective view of a second embodiment device according to the invention in position on a flat surface, such as the skin; and, FIG. 6 is a plane view of the device of FIG. 5.
Figure 6:
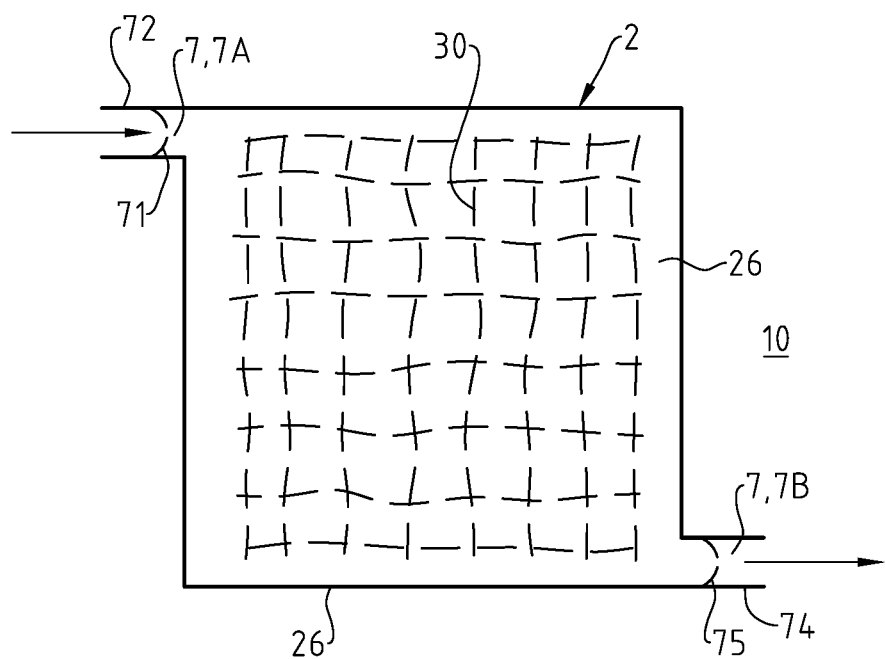

FIGS. 5 and 6 illustrate a second embodiment, adapted to the healing of flat wounds, particularly of skin wounds.

In this second embodiment device 2 is substantially flatly shaped. This device 2 also has one first wall 21 and one second wall 22, the two walls being joined 20 together at their common peripheral portion 26, so that the cavity 24 is provided between the two walls. The cavity is suitable to contain a substance with a healing agent, preferably under pressure. The first wall 21 is tight, so that the substance is prevented to leak through the first wall 21.

The second wall 22 is intended to be in contact with the flat surface 10, while the first wall is also a protection for a wounded area 101 of the flat surface 10 against environmental aggressions. The second wall 22 comprises a porous portion 25, in contact with the wounded area 101, and designed to let the healing agent seep through, to dispense it to the wounded area.

The porous portion 25 is surrounded by a peripheral tight portion 26, said peripheral portion preferably having an adhesive face to maintain the porous part against the wounded area.

In the flat arrangement of FIG. 5, the adhesive portion of the second wall is peripheral to the cavity, and its porous portion covers a whole side of the cavity. In the flat arrangement of FIG. 6, the adhesive portion of the second wall is disposed between the cavity and the flat surface, so that the porous portion covers only partially this side of the cavity.

Advantageously, the first wall is resilient 30, so as, when the cavity contains some substance, the first wall exerts a pressure on the substance in the cavity, the pressure being sufficient for the substance to peer through the porous portion.

The device, as shown in FIG. 5, is provided with means 7 to fill up the cavity. Those means comprise first and second filling means 7A,7B. The first filling means 7A comprise a feeding pipe portion 72 to connect a feeding catheter (not shown) and a valve 71, to prevent leaking of substance, through the pipe portion 72, after filling of the cavity 24. The second filling means 7B comprise a discharge pipe portion 74 and a discharge valve 75. When a sufficient pressure is reached in the cavity 24, the valve is designed to open, so that, in particular, an excess quantity of substance is released through the discharge pipe 74.

The agent filled up in the cavity is preferably a suspension of cells. The suspension of cells can also comprise healing compounds. It is particularly preferred that the cells in suspension are gingival fibroblasts.

Advantageously, gingival fibroblasts have been shown to treat arterial-remodelling pathologies (WO 2006/013261) and more recently to promote and to accelerate skin wound healing. Advantageously also, gingival fibroblasts are easily sampled and cultured. Besides, gingival fibroblasts possess a high expansion rate. Accordingly, gingival fibroblasts provide for an almost limitless source of autologous fibroblasts.

It is also preferred that the cells used for cell therapy are autologous, that is they are taken from the individual to whom they are intended to be administered. Preferably the individual is a mammal and more preferably a human. However, the cells can also be allogenic, that is taken from another individual of the same species or heterologous, that is taken from another individual of another species.

The number of cells in the device should preferably be of from $10^5$ to $10^9$/ml. The volume of the cavity when it is filled is preferably such that the agent filled up in the cavity is under pressure, so that it tends to migrate in direction of the defect, optionally through the porous wall. Preferably, the volume is of from 100 µl to 20 ml.

The implantation procedure of the device of the invention will be apparent to one of skill in the art.

For instance, for skin wounds, the porous wall of the device is apposed onto the wound and maintained in close contact for instance through adhesive means. As regards, the implantation of the device of the invention in vessels, one skilled in the art can for instance follow the general procedure adopted for stent implantation. Briefly, a sheath is inserted in the femoral artery and then a wire is advanced through the aorta. Thereafter, the catheter carrying the device is advanced over the wire until it reaches the desired site.

It shall be evident to a man skill in the art, that the many arrangements and embodiments, not precisely set forth, could be practiced under the teachings of the present invention, as set forth in the following claims.

For example, the use of a stent is not obligatory required. Thus, the internal wall may be sufficiently resilient to expend progressively, as the cavity is emptying, thus maintaining a sufficient pressure in the cavity to cause the substance to seep through the porous portion 25, and to maintain the internal wall 22 against the wall 4 of the vessel.

Preferably, the stent is made of a resorbable matter, such as polylactic acid. If not resorbable, the stent may be made of steel or Nitrinol.

Depending on the indications, the second wall can be omitted. Then the cavity is formed between the tissue and the first tight wall.

In a preferred embodiment, the above-defined device is suitable for a single use only, i.e. it cannot be re-used a second time when it has already been used for cell therapy in an individual.

The invention claimed is:

1. A device for cell therapy, said device being designed to be applied on a living tissue of a biological conduit or a hollow organ and having at least a biocompatible first wall which forms a cavity between said first wall and said tissue, and further comprising:
    means to feed a healing substance into said cavity; and
    a second wall comprising at least a porous part, the cavity being provided between said first and second walls, the healing substance being administered through said porous part, wherein the healing substance in the cavity is a suspension of cells, said second wall being bioresorbable; wherein said device comprising a generally tubular shape, the first wall being a tight internal wall, and the second wall being an external wall, and a stent provides a radial expansion of the device to bring an outward radial pressure on the internal wall so as to urge said internal wall toward said external wall, and the internal wall exerts a pressure on the suspension of cells, the pressure being sufficient for the suspension of cells to move through the porous part of the second wall while allowing fluid flow in the biological conduit or the hollow organ during treatment;
    wherein said means to feed comprises a valve to connect a feeding catheter to supply the suspension of cells and, after feeding, to prevent the supplied suspension of cells to leak through said means to feed.

2. The device according to claim 1, wherein the suspension of cells are gingival fibroblasts.

3. A method for treating a patient in need of cell therapy, wherein a therapeutically effective quantity of cells suitable for said cell therapy is administered with a device according to claim 2.

4. The device according to claim 1, wherein the stent is autoexpandable.

5. The device according to claim 1, wherein the means to feed the suspension of cells is in place during treatment.

6. A method for treating defects of biological conduits or of hollow organs in a patient, comprising:
    implanting a device according to claim 1 at a site of defect of a biological conduit or of a hollow organ;
    filling said device with a suspension of cells suitable to treat said defect; and
    maintaining the device in place at least for a time sufficient for a therapeutically effective quantity of cells to have migrated in direction of the defect and/or for the cells to have exerted a therapeutically effective paracrine effect.

7. The method according to claim 6, wherein the defect is a vascular defect.

8. The method according to claim 6, wherein the cells suitable to treat the defect are gingival fibroblasts.

9. The method according to claim 6, wherein a filling of the cavity is made during treatment.

* * * * *